(12) United States Patent
Mannion et al.

(10) Patent No.: US 10,905,577 B2
(45) Date of Patent: Feb. 2, 2021

(54) STENT DELIVERY SYSTEM

(71) Applicant: COVIDIEN LP, Mansfield, MA (US)

(72) Inventors: Madeline A. Mannion, Beverly, MA (US); Deepankar Ayyagari, Burbank, CA (US); John O. McWeeney, Brighton, MA (US); Olivia P. Metcalf, Somerville, MA (US)

(73) Assignee: Covidien LP, Mansfield, MA (US)

( * ) Notice: Subject to any disclaimer, the term of this patent is extended or adjusted under 35 U.S.C. 154(b) by 81 days.

(21) Appl. No.: 15/897,731

(22) Filed: Feb. 15, 2018

(65) Prior Publication Data

US 2018/0311058 A1 Nov. 1, 2018

Related U.S. Application Data

(60) Provisional application No. 62/491,798, filed on Apr. 28, 2017.

(51) Int. Cl.
*A61F 2/962* (2013.01)
*A61F 2/90* (2013.01)
(Continued)

(52) U.S. Cl.
CPC ............ *A61F 2/962* (2013.01); *A61F 2/90* (2013.01); *A61F 2/97* (2013.01); *A61L 29/04* (2013.01);
(Continued)

(58) Field of Classification Search
CPC ...... A61F 2/82; A61F 2/86; A61F 2/90; A61F 2/92; A61F 2/95; A61F 2/962;
(Continued)

(56) References Cited

U.S. PATENT DOCUMENTS 4,402,685 A 9/1983 Buhler et al.
5,824,054 A * 10/1998 Khosravi .................. A61F 2/92
623/1.44
(Continued)

FOREIGN PATENT DOCUMENTS

CN 101166552 A 4/2008
CN 104053405 A 9/2014
(Continued)

OTHER PUBLICATIONS

Notice of Reason for Rejection dated Feb. 19, 2019 for Japanese Patent Application No. 2018-074630 from the Japanese Patent Office.
(Continued)

*Primary Examiner* — Jocelin C Tanner
(74) *Attorney, Agent, or Firm* — Holland & Hart LLP

(57) ABSTRACT

Methods, apparatuses and systems are described for deploying a stent into a body lumen. A stent delivery system may include a sheath with a partially-tubular first portion made from a first material and a second portion made from a second material that is adhered to the first portion to form a tubular body. In some cases, the first material may be chemically incompatible with the second material such that the adhesion between the first portion and second portion is free from cross-linked bonds. The stent delivery system may further include a guidewire lumen with a distal tip that may be slidably disposed within the sheath and a tubular stent disposed between the guidewire lumen and an inside surface of the sheath. The sheath may be formed by coextruding the first material and the second material to form a striped tubular body of the sheath.

10 Claims, 12 Drawing Sheets

(51) Int. Cl.
*A61M 25/00* (2006.01)
*A61L 29/04* (2006.01)
*A61F 2/97* (2013.01)
*A61L 29/14* (2006.01)
*A61F 2/95* (2013.01)

(52) U.S. Cl.
CPC ......... *A61L 29/14* (2013.01); *A61M 25/0012* (2013.01); *A61F 2/9517* (2020.05); *A61F 2250/0093* (2013.01); *A61F 2250/0097* (2013.01)

(58) Field of Classification Search
CPC ..... A61F 2250/0093; A61F 2250/0097; A61L 29/04; A61L 29/14; A61M 25/0012; A61M 25/0053; A61M 25/008
See application file for complete search history.

(56) References Cited

U.S. PATENT DOCUMENTS

| | | | | |
|---|---|---|---|---|
| 8,048,034 | B2* | 11/2011 | Eversull | A61M 25/0668 604/172 |
| 8,790,387 | B2 | 7/2014 | Nguyen et al. | |
| 2004/0153049 | A1* | 8/2004 | Hewitt | A61M 25/0012 604/527 |
| 2008/0208128 | A1* | 8/2008 | Guo | A61M 25/0668 604/164.05 |
| 2008/0255580 | A1 | 10/2008 | Hoffman et al. | |
| 2010/0268196 | A1* | 10/2010 | Hastings | A61M 25/0668 604/527 |
| 2012/0172887 | A1 | 7/2012 | Hatfield et al. | |
| 2013/0123714 | A1 | 5/2013 | Weber et al. | |
| 2013/0253417 | A1* | 9/2013 | Dinh | A61M 25/0012 604/28 |
| 2014/0157573 | A1 | 6/2014 | Guo et al. | |
| 2014/0188211 | A1 | 7/2014 | Roeder et al. | |
| 2015/0164669 | A1 | 6/2015 | Parker et al. | |
| 2017/0043122 | A1 | 2/2017 | Mannion et al. | |
| 2018/0233252 | A1 | 8/2018 | Esseghir et al. | |

FOREIGN PATENT DOCUMENTS

| | | | |
|---|---|---|---|
| CN | 108028101 | A | 9/2014 |
| EP | 2749258 | A1 | 12/2013 |
| JP | 63252169 | | 10/1988 |
| JP | 27670 | | 2/1990 |
| JP | 668760 | | 9/1994 |
| JP | 2003535642 | | 12/2003 |
| JP | 2004508135 | | 3/2004 |
| JP | 2005185400 | | 7/2005 |
| JP | 2005523126 | A | 8/2005 |
| JP | 2005533557 | | 11/2005 |
| JP | 2008543440 | | 12/2008 |
| JP | 2014516691 | | 7/2014 |
| JP | 2008539048 | A | 11/2018 |
| WO | WO-01097715 | A1 | 12/2001 |
| WO | WO-02022053 | A2 | 3/2002 |
| WO | WO-03090835 | A1 | 11/2003 |
| WO | WO-2006116720 | A2 | 11/2006 |
| WO | WO-2006138356 | A2 | 12/2006 |
| WO | 2014179767 | A3 | 11/2014 |
| WO | 2016164082 | A1 | 10/2016 |

OTHER PUBLICATIONS

Examination Report No. 1 for Australian App. No. 2018201246 dated Sep. 27, 2018 from the Australian Government IP Australia.
Extended European Search Report dated Sep. 21, 2018 for Application No. 18169789.7 from European Patent Office.
Examiner's Report for Canadian App. No. 2,996,908 dated Feb. 18, 2019 from the Canadian Intellectual Property Office.
Second Office Action for CA Application No. 2,996,908, dated Oct. 10, 2019, 5 pgs., Canadian Intellectual Property Office (CIPO).
First Office Action for CN Application No. 201810356763.8, dated Feb. 8, 2019, 10 pgs., China National Intellectual Property Administration (CNIPA).
Notice of Reasons for Rejection for JP Application No. 2018-074630, dated Nov. 6, 2019, 12 pgs., Japan Patent Office (JPO).
Third Office Action for CA Application No. 2,996,908, dated May 1, 2020, 5 pgs. Canadian Intellectual Property Office (CIPO).
Chinese Office Action dated Jun. 11, 2020.
Japanese Final Office Action dated Jul. 28, 2020, Papent Application No. 2018-074630.

* cited by examiner

STENT DELIVERY SYSTEM

CROSS REFERENCE TO RELATED APPLICATION

The present application claims the benefit of and priority to U.S. Provisional Application Ser. No. 62/491,798, filed on Apr. 28, 2017 the entire contents of which are incorporated herein by reference.

BACKGROUND

Diseases and disorders of the gallbladder, pancreas, and bile ducts (i.e., pancreaticobiliary system) are associated with significant morbidity, mortality, and impaired quality of life. Obstructions, tumors, injuries, leakages, inflammation, infection, and lesions can occur in these structures, which can eventually lead to conditions such as biliary colic, cholecystitis, choledocholithiasis, cholelithiasis, pancreatitis, pancreatic duct stone formations, and chronic abdominal pain. Diseases of the pancreaticobiliary system may also be associated with nutritional disorders, such as malnutrition, obesity, and high cholesterol.

To treat a biliary obstruction, a clinician may perform a stent delivery procedure to place a stent across the obstruction. In general, a stent delivery procedure may include placing an endoscope into the gastrointestinal tract and accessing the bile duct with a catheter. A guidewire may then be deployed through the catheter and into the bile duct. Once the guidewire is in place, a stent or other treatment device may be advanced over the guidewire into the bile duct. After the stent is placed in the bile duct, the clinician may withdraw the stent delivery system.

In some instances, it may be difficult to deploy the stent across the biliary obstruction or remove the stent delivery system from the patient. For example, if the clinician accesses the bile duct through the biliary wall, it may be difficult to accurately position the stent due to the distance between the access site and the obstruction relative to the size of the stent delivery system. Similarly, it may be difficult to withdraw the stent delivery system back through the access site due to the size limitations of the access site relative to the size of the stent delivery system.

SUMMARY

The described features generally relate to methods, systems, and devices for deploying a stent within the body lumen. The techniques described herein may be applied to treat diseases of the pancreaticobiliary system, for example. A sheath for deploying the stent within the body lumen is described. A sheath may include a partially-tubular first portion comprising a first material. The sheath may also include a second portion comprising a second material adhered to the first portion to form a tubular body, where the first material is chemically incompatible with the second material such that the adhesion between the first portion and second portion is free from cross-linked bonds.

In some embodiments, the second portion is oriented as a stripe along a longitudinal axis of the tubular body. The first material may comprise polyether block amide (PEBA) and the second material may comprise high-density polyethylene (HDPE). The sheath may further include a tubular liner bonded within the tubular body of the sheath, where the tubular liner comprises polytetrafluoroethylene (PTFE). In some cases, a length of the tubular liner is less than a length of the tubular body.

A sheath for deploying the stent within a body lumen may include a reinforcing element coupled with the first portion of the sheath. In some embodiments, the reinforcing element comprises a partially-tubular body with a channel that aligns with the second portion. In some cases, the reinforcing element comprises a coiled frame. Additionally or alternatively, the reinforcing element comprises a braided frame.

A stent deployment system for deploying the stent within a body lumen is described. A stent deployment system may include a sheath that includes a partially-tubular first portion comprising a first material and a second portion comprising a second material adhered to the first portion to form a tubular body, where the first material is chemically incompatible with the second material such that the adhesion between the first portion and second portion is free from cross-linked bonds. A stent deployment system may further include a guidewire lumen slidably disposed within the sheath, where the guidewire lumen comprises a distal tip with an outer diameter that is greater than an inner diameter of the tubular body. A stent deployment system may also include a tubular stent disposed between the guidewire lumen and an inside surface of the sheath and a guidewire slidably disposed within the guidewire lumen.

A method for forming a sheath is described. The method may include coextruding a first material and a second material to form a striped tubular body, where the striped tubular body comprises a partially-tubular portion and a striped portion. In some cases, the partially-tubular portion comprises the first material and the striped portion comprises the second material, where the first material is chemically incompatible with the second material such that an adhesion between the partially-tubular portion and the striped portion is free from cross-linked bonds. The method may further include positioning a tubular liner within the striped tubular body and wrapping the tubular body in a heat shrink tubing. The method may also include reflowing the striped tubular body and the tubular liner and removing the heat shrink tubing and at least a portion of the striped portion of the tubular body.

In some embodiments, the first material comprises PEBA, the second material comprises HDPE, and the tubular liner comprises PTFE. In some cases, a length of the tubular liner is less than a length of the striped tubular body.

The method of forming a sheath may include removing the striped portion of the tubular body that overlaps the tubular liner. The method may further include positioning a reinforcing element between the tubular liner and the tubular body before wrapping the tubular body in the heat shrink tubing. The method may also include adhering the reinforcing element into the tubular body after wrapping the tubular body in the heat shrink tubing. In some cases, the reinforcing element comprises a partially-tubular body with a channel that aligns with the striped portion. In some embodiments, the method may include removing all of the striped portion to form a channel along the tubular body.

Certain embodiments of the present disclosure may include some, all, or none of the above advantages or features. One or more other technical advantages or features may be readily apparent to those skilled in the art from the figures, descriptions, and claims included herein. Moreover, while specific advantages or features have been enumerated above, various embodiments may include all, some, or none of the enumerated advantages or features.

Further scope of the applicability of the described methods and systems will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
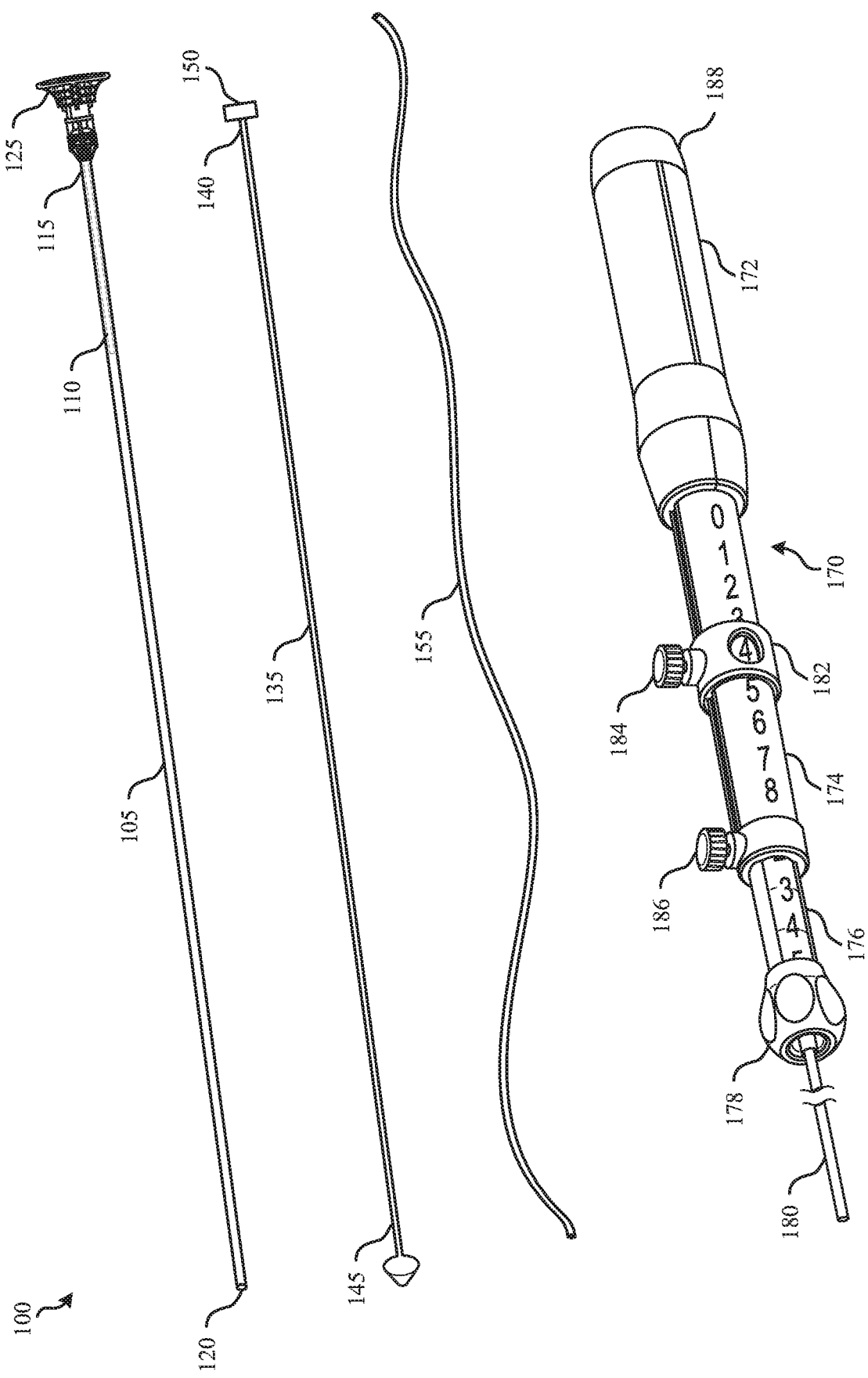
FIG. 1 illustrates an exploded view of a system for providing access to a body lumen in accordance with aspects of the present disclosure.

The present disclosure is generally directed towards a stent delivery system configured to deploy a stent within a body lumen. The stent delivery system may include a sheath that houses an expandable stent. Once in the body lumen, the sheath may be configured to split along its longitudinal direction to allow the stent to expand and deploy from the sheath. The sheath may be made from two chemically incompatible materials such that the materials adhere together, but do not completely bond (e.g., do not form any cross-linked bonds). For example, the sheath may be made from a partially-tubular first portion of a first material and a second portion of a second material adhered to the first portion to form a tubular body. The first material may be chemically incompatible with the second material such that the adhesion between the first portion and second portion allows for the sheath to tear along the adhesion site.

In accordance with aspects of the present disclosure, to place a stent within a body lumen, the luminal wall may be pierced and a stent delivery system may be advanced through the hole (i.e., access site) and positioned at the target site (e.g., across an obstruction). To deploy the stent from the stent delivery system, a portion of the stent delivery system may be engaged to tear the sheath, thereby releasing an expandable stent from the sheath. The stent delivery system may then be withdrawn back out of the lumen through the same hole.

Apparatuses, systems, and methods are described herein for deploying a stent within the body lumen. For example, the stent may be housed in a sheath configured to split along its longitudinal direction and deploy the stent. A guidewire lumen may extend through the sheath and, upon retraction of the guidewire lumen, a distal tip of the guidewire lumen may engage with and split the sheath. To facilitate tearing along a longitudinal direction, the sheath may be made from two chemically incompatible materials that are adhered together along a longitudinal seam. The two-material sheath may be formed through a coextrusion process, which may result in a striped tubular body. In some examples, a liner and/or a reinforcing element may be added to the striped tubular body, and the body may undergo a reflow process to bond the liner and/or the reinforcing elements to the tubular body. In some examples, a portion or all of the striped portion of the body may be removed, thereby forming a channel in the outer layer of the sheath and exposing at least a portion of the inner liner.

Embodiments of the present disclosure are now described in detail with reference to the drawings. As used herein, the term "clinician" refers to a doctor, surgeon, nurse, or any other care provider and may include support personnel. The term "proximal" will refer to the portion of the device or component thereof that is closer to the clinician and the term 'distal" will refer to the portion of the device or component thereof that is farther from the clinician.

FIG. 1 illustrates an exploded view of a system 100 for providing access to a body lumen in accordance with aspects of the present disclosure. The system 100 generally includes a cannula 105, a guidewire lumen 135, a guidewire 155, and a handle assembly 170. The system 100 can be provided as individual components, selectively combined components, or all together as a kit of components. The cannula 105 may be inserted into the handle assembly 170 (through the proximal end 188) until the cannula hub 125 abuts against the proximal end 188. Once assembled, the cannula 105 extends through the handle assembly 170 and through the sheath 180 to the target body lumen.

During a luminal access procedure, the cannula 105 may access the target lumen by piercing a wall of the lumen, for example. In some examples, a sharpened stylet may be used in conjunction with the cannula 105 to facilitate piercing the luminal wall. For example, the sharpened stylet may be advanced through the cannula 105 until it protrudes from the cannula 105 to pierce tissue. Once the cannula 105 has accessed the lumen, the guidewire 155 may be advanced through the cannula 105 and into the lumen. After correct placement of the guidewire 155 inside the body lumen, the guidewire lumen 135 may be advanced over the guidewire 155 and into the body lumen. The guidewire lumen 135 may include a sheath configured to house an expandable stent. As such, the sheath and stent may be advanced over the guidewire 155 and into the body lumen. As discussed in more detail below, the sheath may be configured to split or tear to release the expandable stent into the body lumen.

The system 100 may be used to access and provide treatment to one or more body lumens within the gastrointestinal system or pancreaticobiliary system, for example. It may be appreciated that the system 100 may also be used to provide access or treatment to other organs or luminal systems within the body such as the arterial system, the bronchial system, the urinary system, or any other luminal system were maneuverability and accuracy is desirable.

In some examples described herein, the handle 170 is coupled with an endoscope and the cannula 105 is guided via endoscopic ultrasound (EUS) to provide access to one or more body lumens or organs associated with the pancreaticobiliary system for the purpose of providing treatment. For example, the system 100 may be configured to provide access to at least the common biliary duct to facilitate subsequent procedures to treat narrowed areas or blockages within the bile duct, including palliative drainage procedures. In accordance with various embodiments, the system 100 may be used to perform an Endoscopic Ultrasound Guided Biliary Drainage (EUS-BD) procedure. In a particular embodiment, a palliative drainage procedure may be performed in antegrade fashion in conjunction with the access system 100. In another embodiment, the palliative drainage procedure may be performed in retrograde fashion, referred to as an Endoscopic Retrograde Cholangiopancreatography (ERCP) "Rendezvous" procedure.

The cannula 105 of the system 100 has an elongate tubular body and an internal lumen 110 extending from its proximal end 115 to the distal end 120. In general, the cannula 105 is configured to access a body lumen (e.g., by piercing a luminal wall) and to provide a conduit through which one or more devices (e.g., a guidewire 155) may pass to facilitate subsequent treatment of the body lumen or associate organs. As described with reference to several embodiments, the cannula 105 may include features that facilitate the direction-controlled delivery of a guidewire 155 within the body lumen for subsequent delivery of a stent, a biopsy device, a medicinal delivery element, or any number of other treatment or diagnostic devices.

The guidewire lumen 135 is generally an elongate, tubular member with proximal end 140 and distal end 145, and is dimensioned to slidably advance through the lumen 110 of the cannula 105 and over the guidewire 155. The guidewire lumen 135 may also include a hub 150 coupled with the proximal end 140 of the guidewire lumen 135 to facilitate longitudinal or rotational manipulation of the guidewire lumen 135 with respect to the cannula 105. In certain embodiments, the distal end 145 of the guidewire lumen 135 includes a tip or bulged portion. As described below, the tip at the distal end 145 of the guidewire lumen 135 may be configured to engage with a sheath to tear or otherwise split the sheath along a longitudinal direction. For example, an outer diameter of the tip at the distal end 145 may be greater than an inner diameter of the sheath. As such, the guidewire lumen 135 may be retracted proximally through a lumen of the sheath, which may cause the sheath to stretch and tear.

The guidewire 155 is generally a flexible elongate member configured to slidably advance through the lumen 110 of the cannula 105. The guidewire 155 may be uniform in size and stiffness along its entire length, or alternatively, may include sections of differing stiffness.

The handle assembly 170 is generally configured to facilitate manipulation of the cannula 105, the guidewire lumen 135, and the guidewire 155 with respect to each other, the accessed body lumen, or an attached endoscope. The handle assembly 170 may include a proximal handle member 172 with a proximal portion 188, a middle handle member 174, and a distal handle member 176. The proximal, middle, and distal handle members 172, 174, 176 each include an inner lumen and are coupled together to form a continuous lumen extending throughout the length of the handle assembly 170. The proximal handle member 172 is slidably disposed over at least a portion of the middle handle member 174, and, similarly, the middle handle member 174 is slidably disposed over at least a portion of distal handle member 176. The distal handle member 176 may also include a threaded connector element 178 configured to securely attach to a working channel of an endoscope (not shown).

One or more of the handle members 172, 174, and 176 of the handle assembly 170 may be configured to manipulate one or more components of a stent delivery system. For example, a distal hub may be configured to advance and retract an outer tube that is sized to slide over a stent delivery sheath. For example, upon proximal retraction of the distal hub, the outer tube may slide proximally with respect to the sheath, which may allow deployment of all or part of a stent housed within the sheath. Similarly, a proximal hub may be configured to advance and retract the guidewire lumen 135 with respect to the sheath. For example, upon proximal retraction of the proximal hub, the guidewire lumen 135 may retract proximally through the lumen of the sheath, which may cause the sheath to tear or split longitudinally. A middle hub may be configured to advance and retract the sheath itself. As such, the middle hub may facilitate advancement of the sheath and manipulation of the sheath with respect to a body lumen.

The handle assembly 170 may also include an elongate sheath 180 extending from the distal end of the distal handle member 176. The elongate sheath 180 is generally made from a flexible polymeric material and provides a continuous conduit through which the cannula 105 or other elements (e.g., a stent delivery system or stent delivery sheath) may travel between the handle assembly 170 and the target tissue within the body (e.g., the bile duct). Accordingly, the length and diameter of the elongate sheath 180 may depend upon the particular application.

The handle assembly 170 may also include one or more adjustment features that limit the sliding movement of the handle members 172, 174, 176 relative to each other. For instance, the handle assembly 170 may include a locking ring 182 with a threaded thumbscrew 184 disposed around the middle handle member 174. The locking ring 182 may be slid along the middle handle member 174 and tightened in a desired position with the thumbscrew 184. When tightened, the locking ring 182 limits the movement of the proximal handle member 172 in the distal direction relative to the middle handle member 174, thereby allowing the clinician to establish a set penetration depth of the cannula 105 or guidewire lumen 135 beyond the distal end of the sheath 180. Similarly, a thumbscrew 186 is configured to lock the position of the distal handle member 176 with respect to the middle handle member 174, thereby allowing the clinician to set an extension depth of the elongate sheath 180 beyond the distal end of an attached endoscope.

Figure 2A:
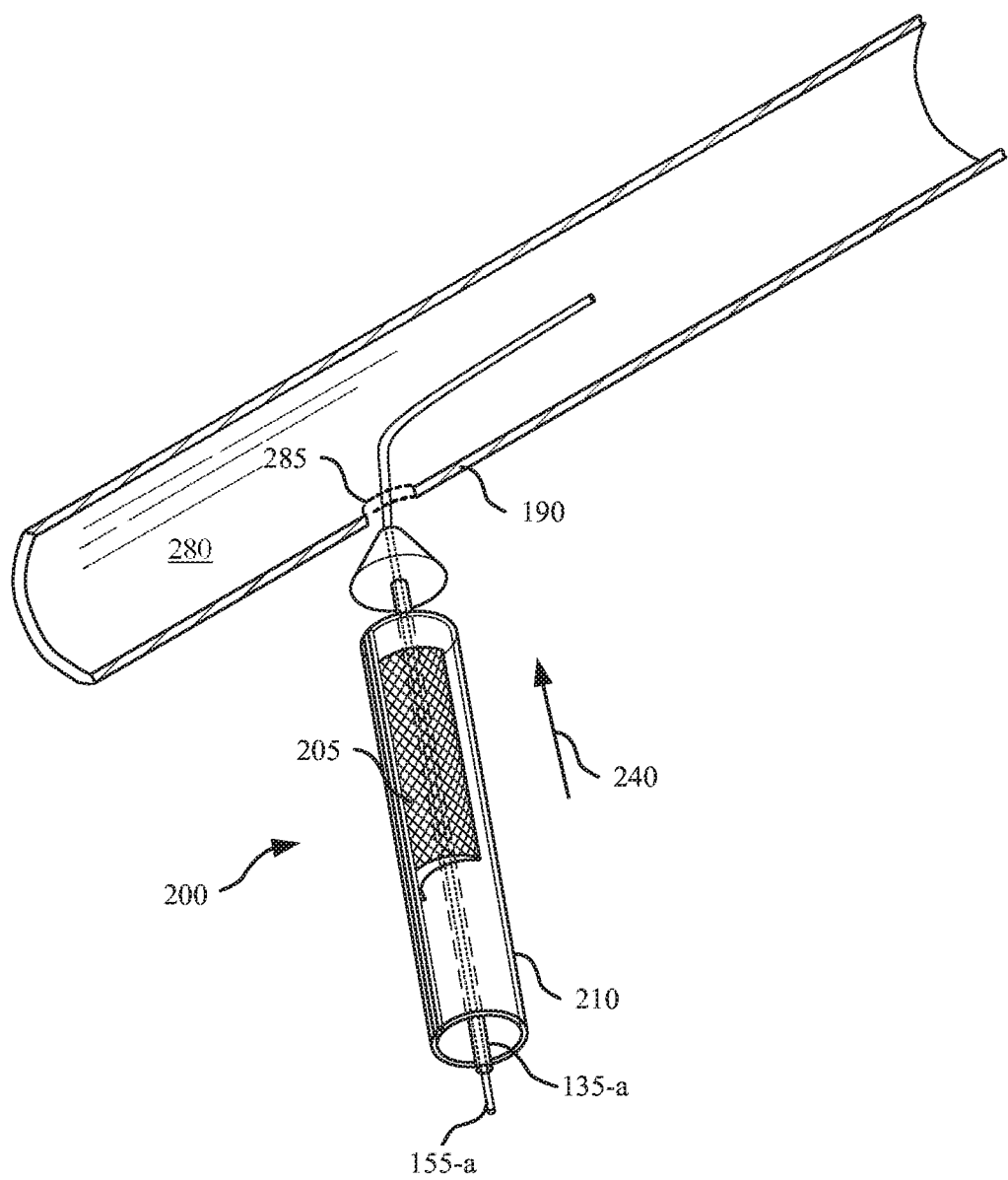
FIG. 2A illustrates a stent delivery system in accordance with aspects of the present disclosure.

FIG. 2A illustrates a stent delivery system 200 in accordance with aspects of the present disclosure. The stent delivery system 200 may be configured to place a stent 205 within a body lumen 280 to restore luminal flow across narrowed areas or blockages within the body lumen 280. The stent delivery system 200 may be sized or otherwise adapted to place a stent 205 within any body lumen 280, such as those associated with the pancreaticobiliary system, the arterial system, the bronchial system, the urinary system, or any other luminal system that may require stent treatment. The stent delivery system 200 may generally include a sheath 210 and guidewire lumen 135-*a*. The guidewire 155-*a* may be part of the stent delivery system 200 or may be a separate component. The stent delivery system 200 can be provided as individual components, selectively combined components, or all together as a kit of components.

The sheath 210 may generally be a tubular structure that is sized to house the stent 205 and deploy the stent 205 within the body lumen 280. The sheath 210 may access the human body through the working channel of an endoscope, for example, as described with reference to FIG. 1. As will be appreciated, the sheath 210 may be made from any number of biocompatible materials or combinations of materials suitable for medical sheaths, catheters, and the like. Furthermore, as discussed in more detail below, the sheath 210 may be made from two chemically incompatible materials such that the two materials may adhere, but may not form cross-linked bonds. As such, the sheath 210 may be configured to tear along the seam between the two materials (e.g., along a longitudinal direction), to deploy the stent 205.

In general, a stent 205 is a frame or scaffolding structure sized for placement within a body lumen 280 and configured to provide structural support to the inner surface of the body lumen 280. A stent 205 may be used to restore patency across narrowed or blocked areas within the body lumen 280 due to inflammation, tumors, plaque buildup, or any other obstructive feature. Although references to the pancreaticobiliary system are provided herein, it should be appreciated that the stents described herein may be used in any body lumen 280.

The stent 205 may be made from any number of materials, combinations of materials, and constructions. For example, the stent 205 may be a braided stent made from a plurality of wires joined together in a cross-hatch configuration. However, it should be appreciated that the stent 205 may be made from other stent constructions or combinations of stent constructions. In other examples, the stent 205 is a laser-cut stent formed from a single metallic tube with regions cut away for increased flexibility. In yet other examples, the stent 205 is a wire-form stent formed by one or more helically wrapped wires. It may be appreciated that the different stent constructions may exhibit particular characteristics such as radial expansive force, flexibility, reduced foreshortening, or migration resistance that may render a certain construction advantageous for a particular use.

The individual wires or frame of the stent 205 may be made from any number of metallic materials including, but not limited to, titanium, nitinol, or stainless steel. It should be appreciated that other metallic or non-metallic materials may be used to construct the stent 205 that provide suitable flexibility, stiffness, and biocompatibility. The stent 205 may include a polymeric or fabric sleeve that covers some or all of the surface of the stent 205. Such a sleeve may protect the inner surface of the body lumen 280 from the bare metal of the stent 205 and may prevent tissue ingrowth. In some examples, the stent 205 is a drug-eluting stent.

Referring still to FIG. 2A, to place the stent delivery system 200 within the body lumen 280, an access hole 285 is formed through the wall 190 of the body lumen 280, and the guidewire 155-*a* is then advanced through the access hole 285 and into the body lumen 280. Once the guidewire 155-*a* is in place, the sheath 210 and guidewire lumen 135-*a* are advanced distally, as indicated by arrow 240, over the guidewire 155-*a*, through the access hole 285, and into the body lumen 280.

Figure 2B:
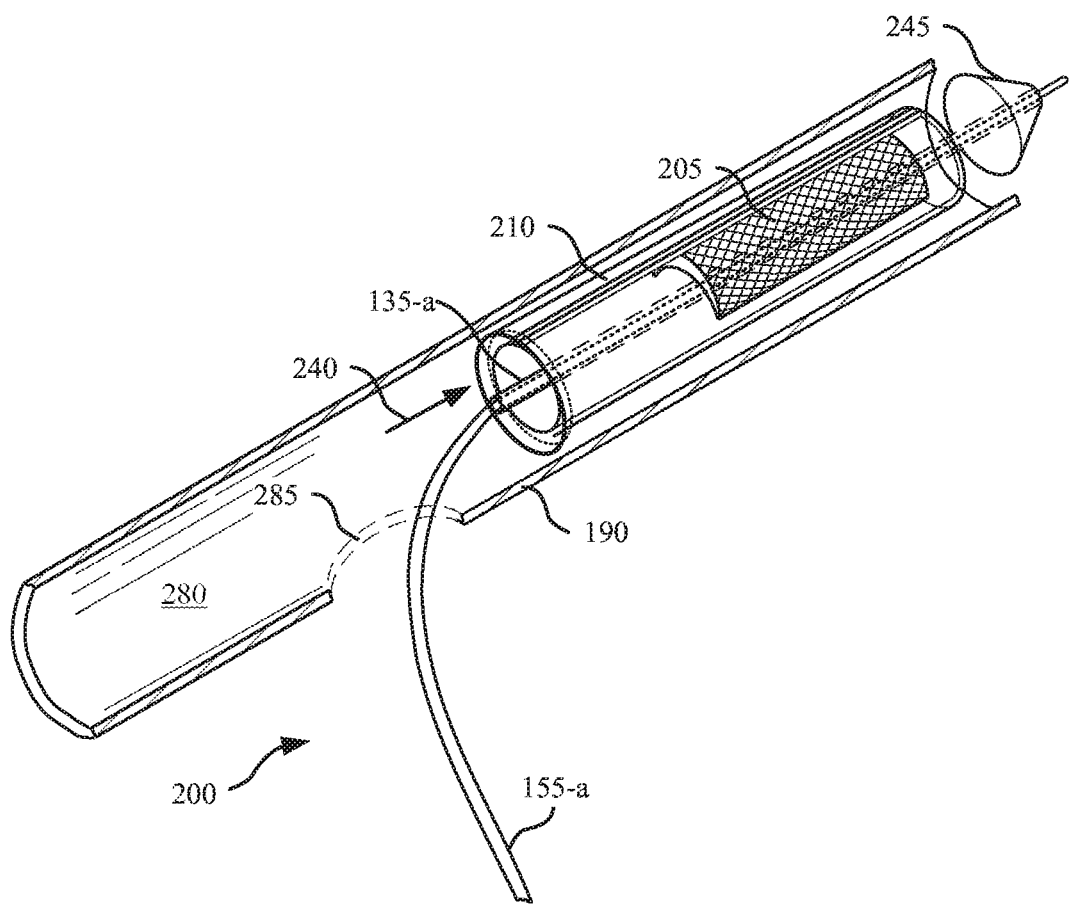
FIG. 2B illustrates a stent delivery system within a body lumen in accordance with aspects of the present disclosure.

FIG. 2B illustrates the stent delivery system 200 of FIG. 2A within the body lumen 280 in accordance with aspects of the present disclosure. Once in the body lumen 280, the sheath 210 may be configured to split longitudinally to allow the stent 205 to expand and deploy from the sheath 210. In some examples described in more detail below, the sheath 210 may be made from two chemically incompatible materials, which may allow the sheath to naturally split along a seam where the two materials join. For example, the guidewire lumen 135-*a* may be proximally retracted through the sheath 210, which may cause the sheath 210 to split if the outer diameter of the distal tip 245 is larger than an inner diameter of the sheath 210. The sheath 210 may include an internal liner that extends a partial or full length of the sheath 210. In other examples, the sheath 210 may not include a liner. Also, in examples that include a full or partial-length liner, all or a portion of the striped portion of the sheath (e.g., a striped portion formed by one of the two chemically incompatible materials) may be removed from the sheath prior to putting the sheath into the body lumen.

Figure 3A:
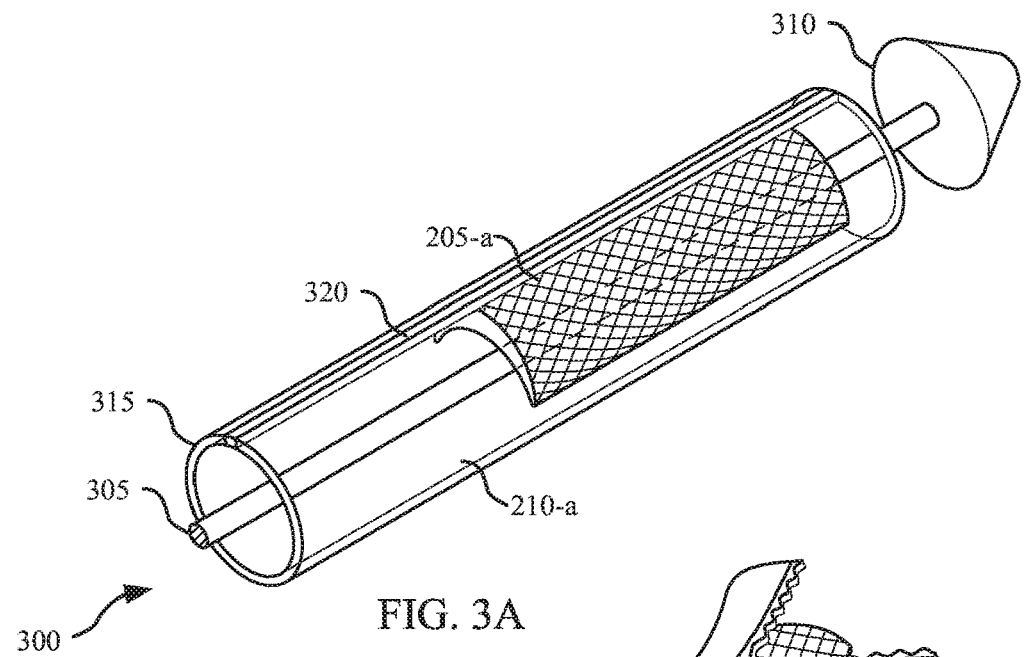
FIG. 3A illustrates a perspective view of a stent delivery system with the stent in a stowed configuration in accordance with aspects of the present disclosure.

FIG. 3A illustrates a perspective view of a stent delivery system 300 with the stent 205-*a* in a stowed configuration in accordance with aspects of the present disclosure. The stent delivery system 300 may be configured to place a stent 205-*a* within a body lumen to restore luminal flow across narrowed areas or blockages within the body lumen. The stent delivery system 300 generally includes a sheath 210-*a*, a stent 205-*a*, and a guidewire lumen 305. The guidewire lumen 305 may include an internal lumen sized to advance over a guidewire 155, and may be an example of guidewire lumen 135-*a*, as described with reference to FIGS. 1-2. Guidewire 155, as described in reference to FIGS. 1-2A, may extend through the lumen of guidewire lumen 305. In some cases, the guidewire lumen 305 may include a distal tip 310. In some examples, the stent 205-*a* may be compressed down and positioned between the inside surface of the sheath 210-*a* and the guidewire lumen 305, which may be referred to as a side-saddle configuration (e.g., as shown in FIG. 3A). That is, in the side-saddle configuration, the guidewire lumen 305 does not extend through the lumen of the stent 205-*a*.

In some cases, the sheath 210-*a* may include a jacket 315. The jacket 315 may refer to a partially-tubular first portion of the sheath 210-*a*. That is, the jacket 315 may form a substantial portion of the tubular body of the sheath 210-*a*, but may not be completely tubular itself. In some cases, the jacket 315 may be sufficiently stiff to resist the radial expansion force of the stent 205-*a* within the sheath 210-*a*. The jacket 315 may be manufactured from a variety of materials such as thermoplastic elastomers. Exemplary thermoplastic elastomer materials include, but are not limited to, polyether block amide (PEBA). For example, the jacket 315 may include a copolymer material with thermoplastic and elastomeric properties. In some examples, the jacket 315 may include a reinforcing element that is fused within the material of the jacket 315 to provide additional radial strength.

The sheath 210-a may include a stripe 320 (also referred to herein as a striped portion of the tubular body of the sheath). The stripe 320 may be oriented along the longitudinal axis of the tubular body of the sheath 210-a. The stripe 320 may adhere to the jacket 315 to form the tubular body of the sheath 210-a. The stripe 320 may be manufactured from a variety of materials such as polymers. Exemplary polymeric-based materials include, but are not limited to, high-density polyethylene (HDPE). For example, the stripe 320 may consist of a material characterized by a chain of unbranched, linear polyethylene polymers.

Figure 3B:
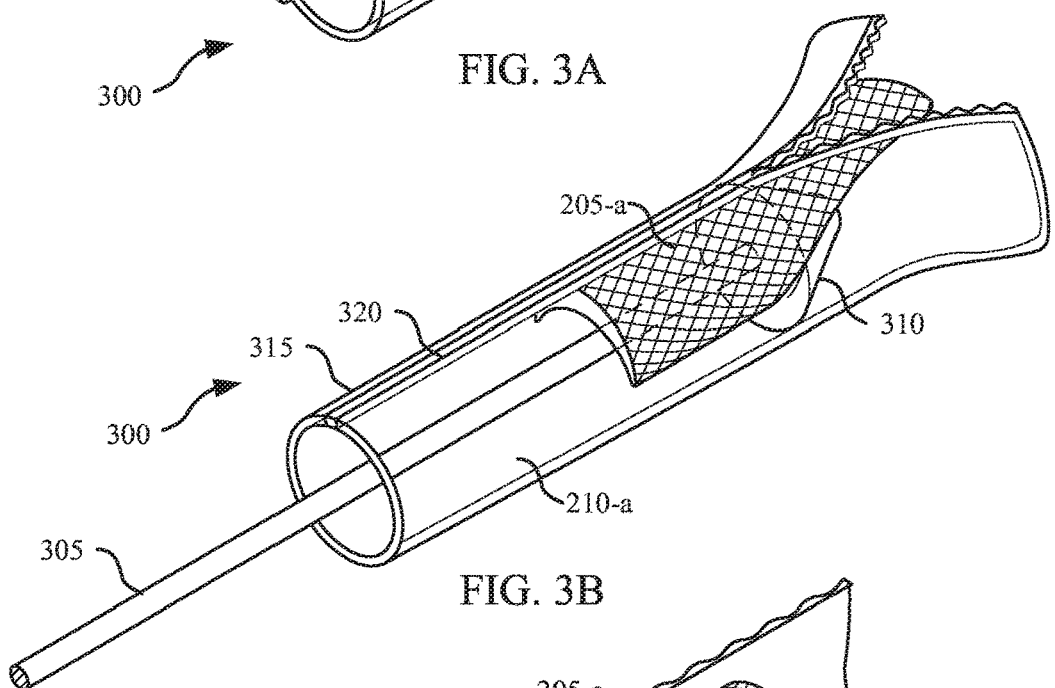
FIG. 3B illustrates a perspective view of the stent delivery system of FIG. 3A with the stent partially deployed in accordance with aspects of the present disclosure.

FIG. 3B illustrates a perspective view of the stent delivery system 300 of FIG. 3A with the stent 205-a partially deployed in accordance with aspects of the present disclosure. The distal tip 310 of the guidewire lumen 305 may be configured to facilitate tearing of the sheath 210-a. For example, an outer diameter of the distal tip 310 may be greater than an inner diameter of the sheath 210-a. As such, as the distal tip 310 is pulled proximally through the sheath 210-a, the distal tip 310 may stretch the sheath 210-a and cause the sheath 210-a to tear. As the sheath 210-a tears, the stent 205-a may begin to deploy from the sheath 210-a and into the body lumen, as illustrated in FIG. 3B. In some examples, the sheath 210-a may be notched to facilitate tearing of the sheath 210-a as the distal tip 310 is retracted in the proximal direction.

In some cases, the proximal end of the stent 205-a may be deployed prior to retraction of the distal tip 310. In some instances, an exterior tube may be located on the proximal end of the stent delivery system 300. The sheath 210-a may include an open pocket or slit at a proximal end of the sheath 210-a where the stent 205-a may partially deploy. For example, the open pocket may be configured to house the stent 205-a when the exterior tube is located on the proximal end of the stent delivery system 300 and deploy the stent when the exterior tube pulled from the proximal end of the stent delivery system 300. When the exterior tube is retracted in the proximal direction, the proximal end of the stent 205-a may deploy through the open pocket of the sheath 210-a. That is, the stent 205-a may cover at least a portion of the puncture site in the body lumen.

In some cases, the material of the jacket 315 may be chemically incompatible with the material of the stripe 320. If the two materials are chemically incompatible, they may adhere together (e.g., as a result of a co-extrusion, re-flow, or similar tube formation process), but the adhesion may not be considered a complete or a chemically compatible bond. For example, due to the different chemical structures of the two chemically incompatible materials, the adhesion between the jacket 315 and the stripe 320 may be free from cross-linked bonds. In some cases, the adhesion between the jacket 315 and the stripe 320 may be free from ionic or covalent bonds. In contrast, if the material of the jacket 315 and the material of the stripe 320 were chemically compatible, the two materials would melt together and would form cross-linked bonds as a result of a heating or reflow process.

Therefore, because of the chemically-incompatible adhesion between the two materials, the retraction of the distal tip 310 in the proximal direction may allow the sheath 210-a to tear along the stripe 320. In other examples, the jacket 315 and the stripe 320 may be comprised of dissimilar materials that lack bondability. For example, the incompatible lamination may be due to different polymer-based chemistries of the jacket 315 and the stripe 320. In addition, a catalyst used to initiate the chemical reaction for the polymerization process to manufacture the material of the jacket 315 and the material of the stripe 320 may be different.

Figure 3C:
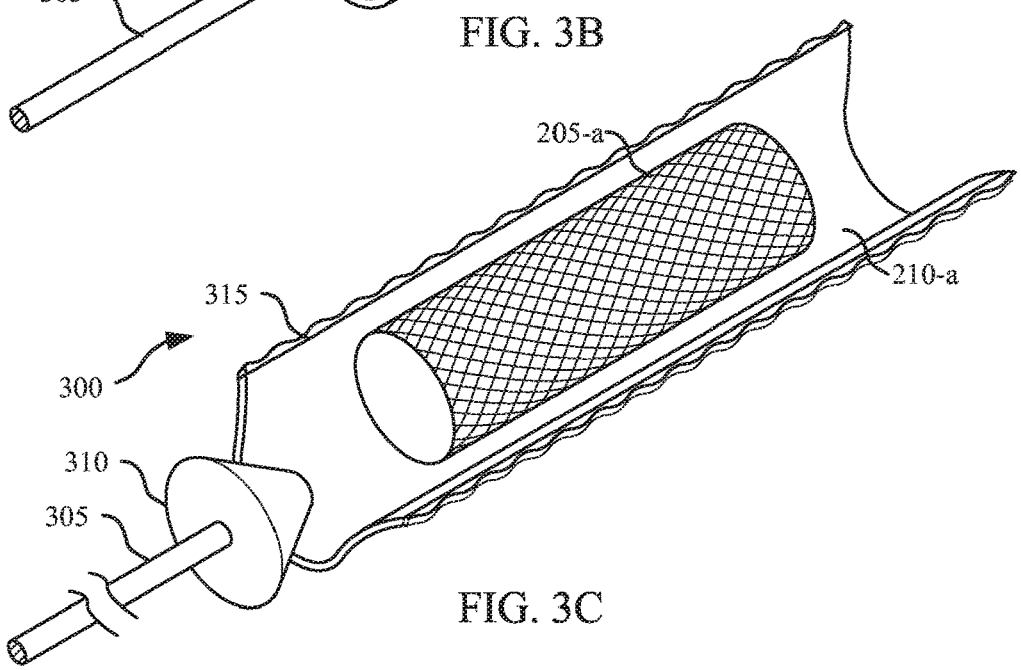
FIG. 3C illustrates a perspective view of the stent delivery system of FIG. 3A with the stent fully deployed in accordance with aspects of the present disclosure.

FIG. 3C illustrates a perspective view of the stent delivery system 300 of FIG. 3A with the stent 205-a fully deployed in accordance with aspects of the present disclosure. In some examples, to fully deploy the stent 205-a from the stent delivery system 300, the guidewire lumen 305 and the distal tip 310 are withdrawn proximally to fully tear the sheath 210-a. After the sheath 210-a is torn, and the stent 205-a is fully expanded within the body lumen, the sheath 210-a may be withdrawn proximally (e.g., back through the access site). Because the stent 205-a is located between the inside surface of the sheath 210-a and the guidewire lumen 305 in a side-saddle configuration, the stent 205 will be pushed from the distal end of the sheath 210-a as the distal tip 310 is withdrawn proximally. In the case of a self-expanding stent, the stent 205-a expands to contact the inner surface of the body lumen as it exits the sheath 210-a.

Figure 4A:
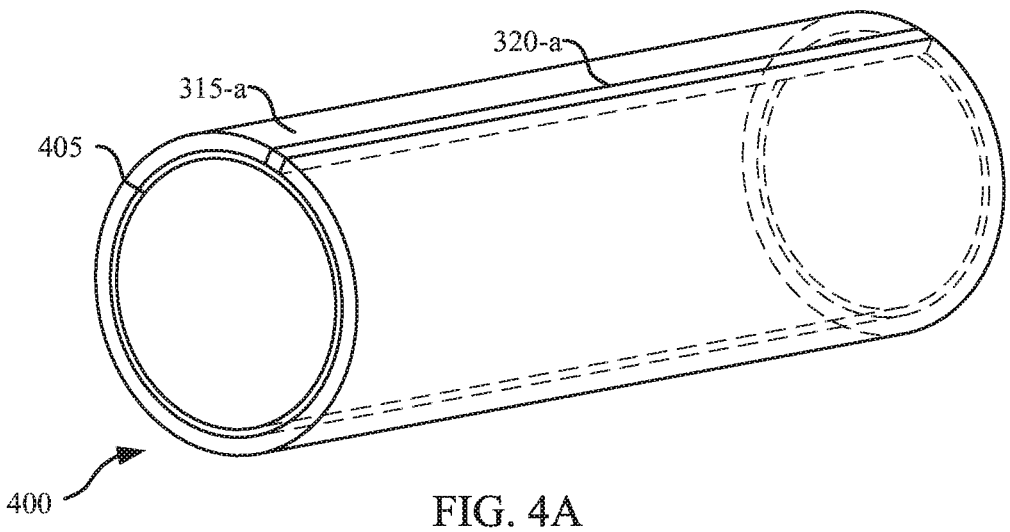
FIG. 4A illustrates a perspective view of a sheath with a liner in accordance with aspects of the present disclosure.

FIG. 4A illustrates a perspective view of a sheath 400 with a liner 405 in accordance with aspects of the present disclosure. As described above, the sheath 400 may be made from two different portions, each made from different materials, such as a jacket 315-a and a stripe 320-a. The sheath 400 may be designed to split along its longitudinal direction between two chemically incompatible materials. The sheath 400 may be an example of a sheath 210 described with reference to FIGS. 2-3. In accordance with various examples, sheath 400 may be used to deploy a stent, as described with reference to FIG. 3.

In some cases, the liner 405 may be disposed within the tubular body of the sheath 400. The length of the liner 405 may be equal to the length of the sheath 400, and the liner 405 may line the full circumference of the tubular body of the sheath 400. The liner 405 may be comprised of a lubricous material that may bond to the material of the jacket 315-a during a reflow or similar melting process. The liner 405 may be comprised of a lubricous material that may not bond to the material of the stripe 320-a. Exemplary materials of the liner 405 include, but are not limited to, polytetrafluoroethylene (PTFE).

Figure 4B:
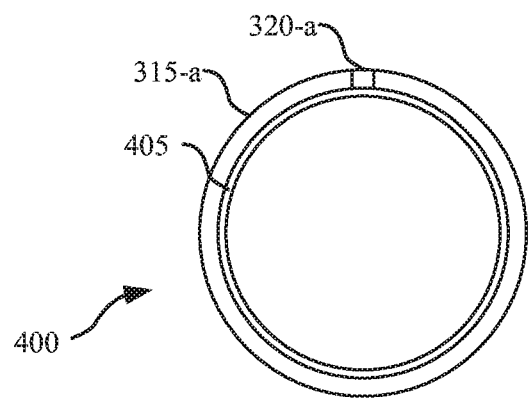
FIG. 4B illustrates a cross-sectional view of the sheath of FIG. 4A in accordance with aspects of the present disclosure.

FIG. 4B illustrates a cross-sectional view of the sheath 400 in accordance with aspects of the present disclosure. The sheath 400 may be manufactured by coextruding the material of the jacket 315-a and the material of the stripe 320-a to form a striped tubular body of the sheath 400. The liner 405 may be positioned within the striped tubular body of the sheath 400. As described in more detail below, to form the sheath 400, the liner 405 may be loaded onto a mandrel (not shown), and the tubular body of the sheath 400 may then be wrapped in a heat shrink tubing.

To bond the liner 405 to the jacket 315-a, the tubular body of the sheath 400 may be reflowed. For example, the striped tubular body of the sheath 400 including the jacket 315-a and the stripe 320-a may be fused together using hot air or a glow ring. In some examples, the liner 405 may bond to the surface of the jacket 315-a. The heat shrink tubing may then be removed, and in some cases, the stripe 320-a may be removed from the tubular body of the sheath 400, thereby forming a channel along the sheath 400 and exposing the liner 405.

Figure 4C:
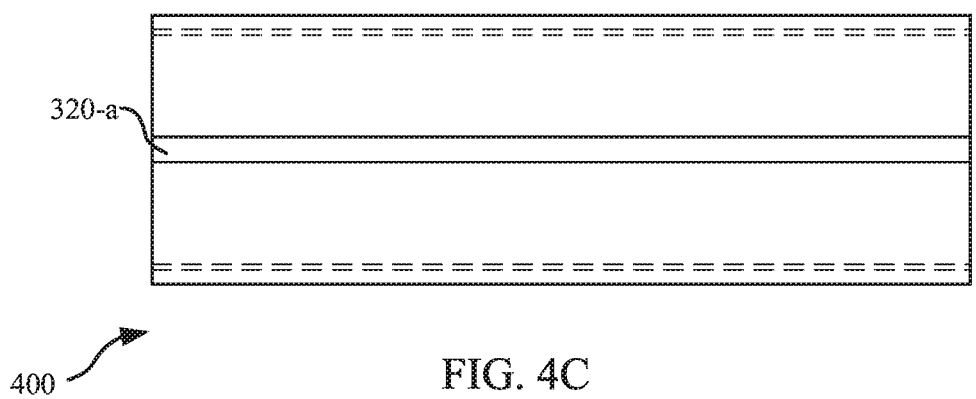
FIG. 4C illustrates a top view of the sheath of FIG. 4A in accordance with aspects of the present disclosure.

FIG. 4C illustrates a top view of the sheath 400 in accordance with aspects of the present disclosure. In some cases, the stripe 320-a may be removed from the sheath 400 prior to implantation in the patient. For example, the stripe 320-a may be removed to expose the liner 405 prior to implantation in the patient. In other examples, the stripe 320-*a* may be kept in the sheath 210-*b* for implantation in the patient. For example, in examples where the liner 405 is absent from the sheath 400, the stripe 320-*a* may be kept as part of the sheath 400 prior to implementation in the patient.

Figure 5A:
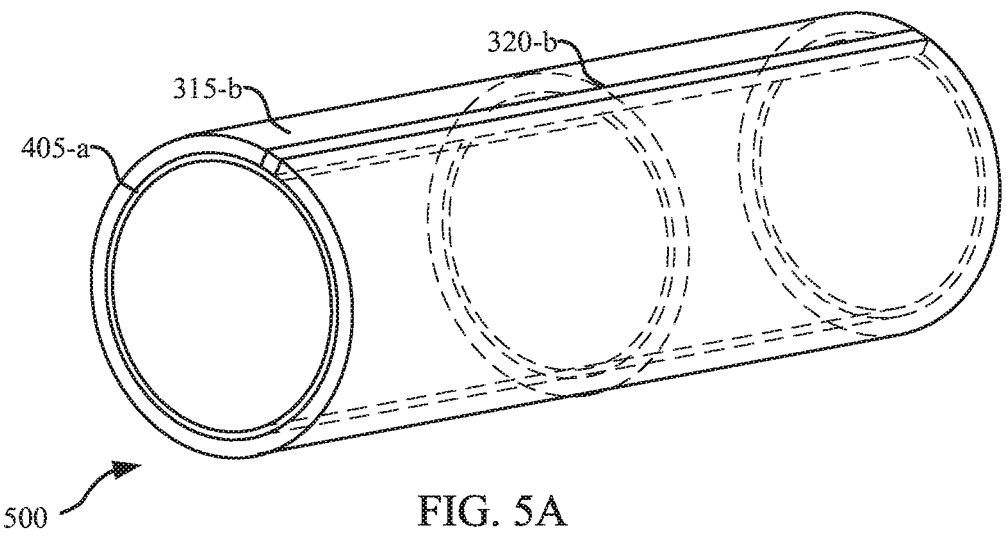
FIG. 5A illustrates a perspective view of a sheath with a partial-length liner in accordance with aspects of the present disclosure.

FIG. 5A illustrates a perspective view of a sheath 500 with a partial-length liner 405-*a* in accordance with aspects of the present disclosure. As described above, the sheath 500 may be made from two different materials such as a jacket 315-*b* and a stripe 320-*b*. The sheath 500 may be designed to split along its longitudinal direction between two chemically incompatible materials. The sheath 500 may be an example of any sheath described above. In accordance with various examples, sheath 500 may be used to deploy a stent, as described with reference to FIG. 3.

In some cases, the liner 405-*a* may be disposed within the tubular body of the sheath 500. The length of the liner 405-*a* may be less than the length of the sheath 500, and the liner 405-*a* may line the full circumference of the tubular body of the sheath 500 for a length less than the length of the sheath 500. The liner 405-*a* may be comprised of a lubricous material that may bond to the material of the jacket 315-*b*. In other cases, the liner 405-*a* may be comprised of a lubricous material that may not bond to the material of the stripe 320-*b*. Exemplary materials of the liner 405-*a* include, but are not limited to, PTFE.

Figure 5B:
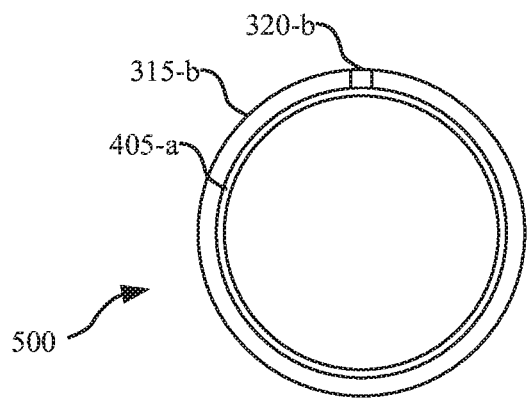
FIG. 5B illustrates a cross-sectional view of the sheath of FIG. 5A in accordance with aspects of the present disclosure.

FIG. 5B illustrates a cross-sectional view of the sheath 500 in accordance with aspects of the present disclosure. The 500 may be manufactured by coextruding the material of the jacket 315-*b* and the material of the stripe 320-*b* to form a striped tubular body of the sheath 500. In some cases, a portion of the liner 405-*a* may be positioned within the striped tubular body of the sheath 500. The liner 405-*a* may be loaded onto a portion of a mandrel (not shown), and the tubular body of the sheath 500 may then be wrapped in a heat shrink tubing in preparation for a reflow process. It may be appreciated that the stripe 320-*b* may overlap with all of or a portion of the liner 405-*a*. In some cases, after the reflow process, the stripe 320-*b* may be removed from the tubular body of the sheath 500 that overlaps with the liner 405-*a*. In such examples, the sheath 500 will have a channel extending the length of the liner 405-*a*, and then will have a solid tubular body for the rest of the length of the sheath 500. The partially-removed stripe 320-*b* may facilitate tearing of the sheath 500, while not requiring that the distal tip of the guidewire lumen (as described with reference to FIG. 3) tear through a length of the liner 405 equal to the length of the sheath 500.

Figure 5C:
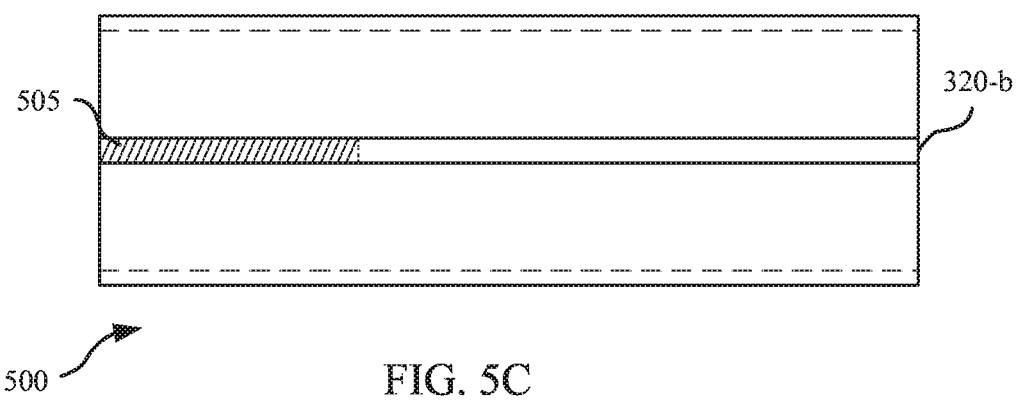
FIG. 5C illustrates a top view of the sheath of FIG. 5A in accordance with aspects of the present disclosure.

FIG. 5C illustrates a top view of the sheath 500 in accordance with aspects of the present disclosure. In some cases, the portion of the stripe 320-*b* that overlaps with the liner 405 may be removed from the sheath 500 prior to implantation in the patient. The stripe 320-*b* may be removed to expose a channel of the liner 405-*a*, as illustrated by liner channel 505. In some cases, the portion of the sheath 500 with the liner 405-*a* may have sufficient radial strength to hold the distal end of the stent within the sheath 500 prior to retraction of the distal tip of a guidewire lumen. Upon retraction of the distal tip, the portion of the sheath 500 with the liner 405-*a* may tear to fully deploy the stent. When the distal tip reaches the portion of the sheath 500 without the liner 405-*a*, the stent may self-deploy due to the radial force of the stent against the sheath 500.

Figure 6A:
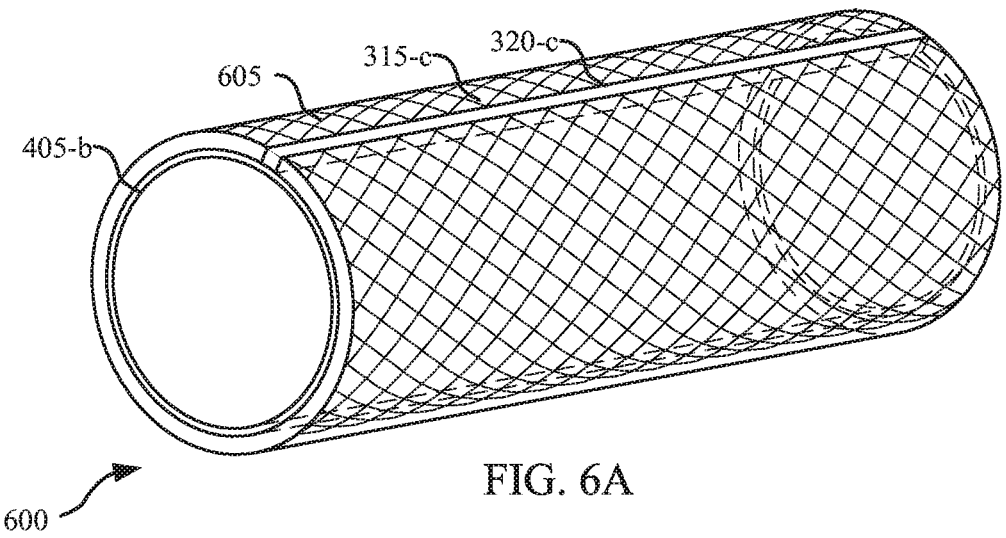
FIG. 6A illustrates a perspective view of a sheath with a reinforcing element in accordance with aspects of the present disclosure.

FIG. 6A illustrates a perspective view of a sheath 600 with a reinforcing element 605 in accordance with aspects of the present disclosure. The sheath 600 may also include a liner 405-*b*. However, in some examples, the sheath may include the reinforcing element 605 instead of the liner 405-*b*. As described above, the sheath 600 may be made of two different materials such as a jacket 315-*c* and a stripe 320-*c*. The sheath 600 may be designed to split along its longitudinal direction between two chemically incompatible materials. The sheath 600 may be an example of any sheath described above. In accordance with various examples, sheath 600 may be used to deploy a stent, as described with reference to FIG. 3.

In some cases, the liner 405-*b* may be disposed within the tubular body of the sheath 600. As described above, the length of the liner 405-*b* may be equal to the length of the sheath 600, or may be less than a length of the sheath 600. The liner 405-*b* may be comprised of a lubricous material that may bond to the material of the jacket 315-*c*. The liner 405-*b* may be comprised of a lubricous material that may not bond to the material of the stripe 320-*c*. Exemplary materials of the liner 405-*b* include, but are not limited to, PTFE.

The reinforcing element 605 may be coupled with a first portion of the jacket 315-*c*, and the reinforcing element 605 may be comprised of a partially tubular body with a channel that aligns with the stripe 320-*c*. The reinforcing element 605 may be made from a braided frame structure. For example, the reinforcing element may be made from a braided tubing that has a channel cut along its longitudinal direction. In some examples, the reinforcing element 605 may be made from a plurality of wires joined together in a cross-hatch configuration. The reinforcing element 605 may be made from a variety of materials, including but not limited to metals (e.g., stainless steel, Nitinol), or a variety of structural polymers.

Figure 6B:
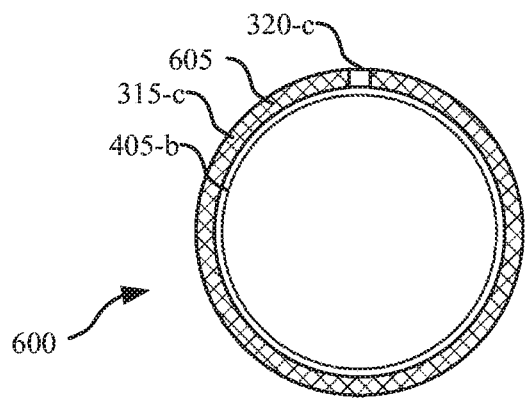
FIG. 6B illustrates a cross-sectional view of the sheath of FIG. 6A in accordance with aspects of the present disclosure.

FIG. 6B illustrates a cross-sectional view of the sheath 600 in accordance with aspects of the present disclosure. As described above, the sheath 600 may be manufactured by coextruding the material of the jacket 315-*c* and the material of the stripe 320-*c* to form a striped tubular body of the sheath 600. In examples with a liner, the liner 405-*b* may be positioned within the sheath 600 and bonded to the striped tubular body of the sheath 600. As part of the formation process, the reinforcing element 605 may be positioned between the liner 405-*b* and the striped tubular body of the sheath 600 before the reflow process. The tubular body of the sheath 600 may then be wrapped in a heat shrink tubing.

To bond the liner 405-*b* to the jacket 315-*c*, the tubular body of the sheath 600 may be reflowed. For example, the striped tubular body of the sheath 600 may be fused together using hot air or a glow ring. In some cases, the material of the jacket 315-*c*, the stripe 320-*c*, and the liner 405-*b* may melt and flow around the reinforcing element 605 during the heating or reflow process. The heat shrink tubing may then be removed, and in some cases, the stripe 320-*c* may be removed from the tubular body of the sheath 600.

Figure 6C:
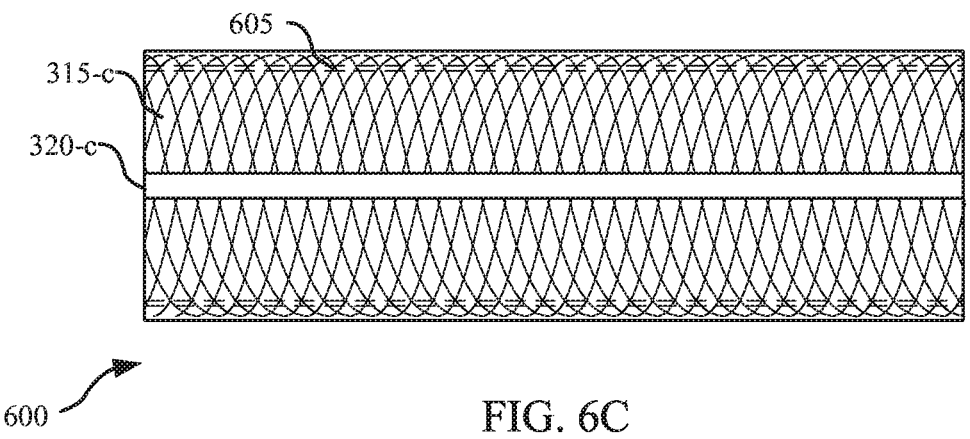
FIG. 6C illustrates a top view of the sheath of FIG. 6A in accordance with aspects of the present disclosure.

FIG. 6C illustrates a top view of the sheath 600 in accordance with aspects of the present disclosure. In some cases, the stripe 320-*c* may be completely or partially removed from the sheath 600 prior to implantation in the patient. In other examples, the stripe 320-*c* may be kept in the sheath 600. As discussed above, the reinforcing element 605 may provide radial strength to help hold the stent within the sheath prior to deployment.

Figure 7A:
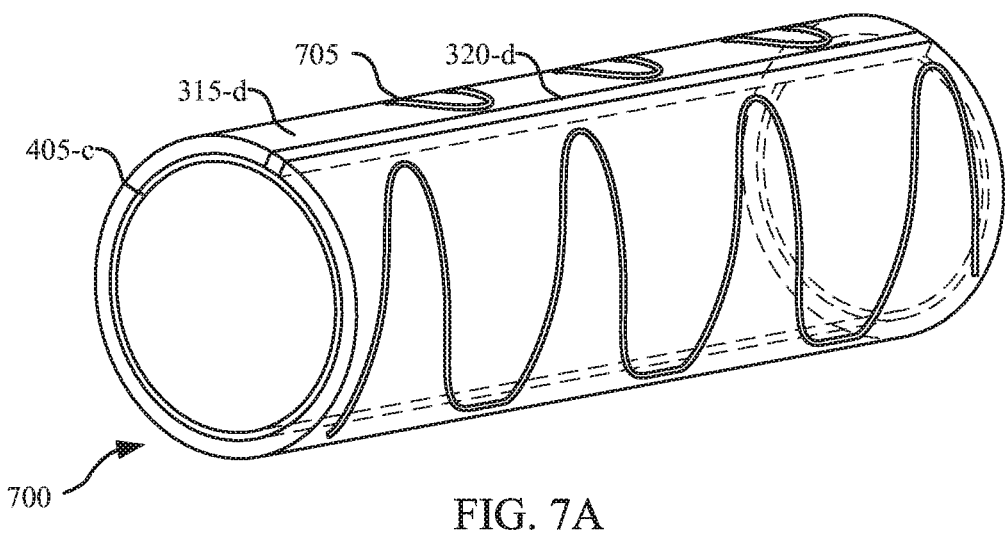
FIG. 7A illustrates a perspective view of a sheath with a reinforcing element in accordance with aspects of the present disclosure.

FIG. 7A illustrates a perspective view of a sheath 700 with a reinforcing element 705 in accordance with aspects of the present disclosure. The sheath 700 may include a liner 405-*c*. However, in some examples, the sheath 700 may include the reinforcing element 705 instead of the liner 405-*c*. As described above, the sheath 700 may be made of two different materials such as a jacket 315-*d* and a stripe 320-*d*. The sheath 700 may be designed to split along its longitudinal direction between two chemically incompatible materials. The sheath 700 may be an example of any sheath described above. In accordance with various examples, sheath 700 may be used to deploy a stent, as described in reference to FIG. 3.

The reinforcing element 705 may be a coiled frame. For example, the coiled frame may be formed by heat setting a Nitinol wire around a mandrel to form a series of S-shapes or C-rings.

Figure 7B:
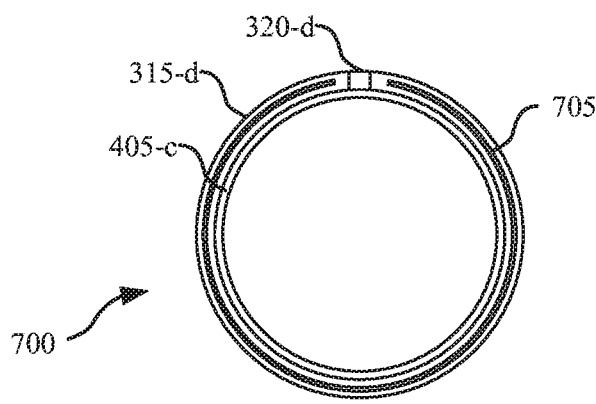
FIG. 7B illustrates a cross-sectional view of the sheath of FIG. 7A in accordance with aspects of the present disclosure.

FIG. 7B illustrates a cross-sectional view of the sheath 700 in accordance with aspects of the present disclosure. The sheath 700 may be manufactured by coextruding the material of the jacket 315-d and the material of the stripe 320-d to form a striped tubular body of the sheath 700. The liner 405-c may be positioned within the striped tubular body of the sheath 700, and the reinforcing element 705 may be fused with the jacket 315-d, stripe 320-d, and liner 405-c with heat shrink tubing and a hot air source. The heat shrink tubing may then be removed.

Figure 7C:
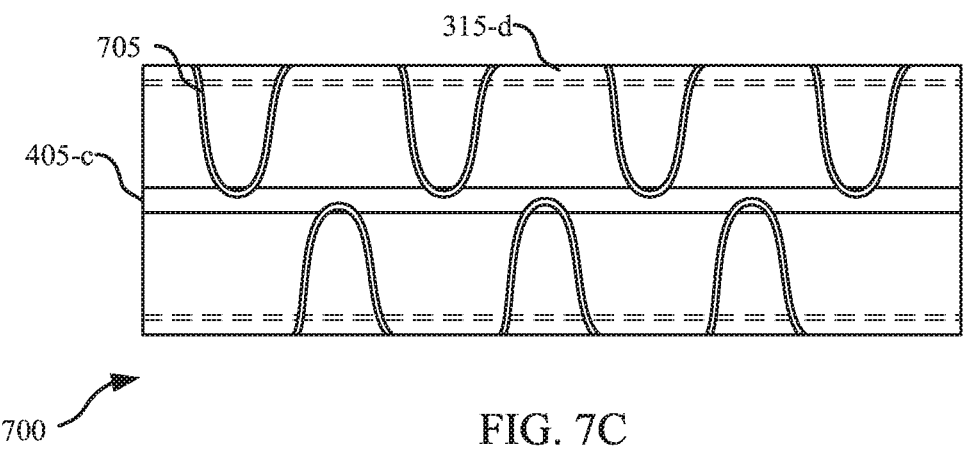
FIG. 7C illustrates a top view of the sheath of FIG. 7A in accordance with aspects of the present disclosure.

FIG. 7C illustrates a top view of the sheath 700 in accordance with aspects of the present disclosure. In some cases, the stripe 320-d may be removed from the sheath 700 prior to implantation in the patient. For example, the stripe 320-d may be removed to expose the liner 405-c.

Figure 8:
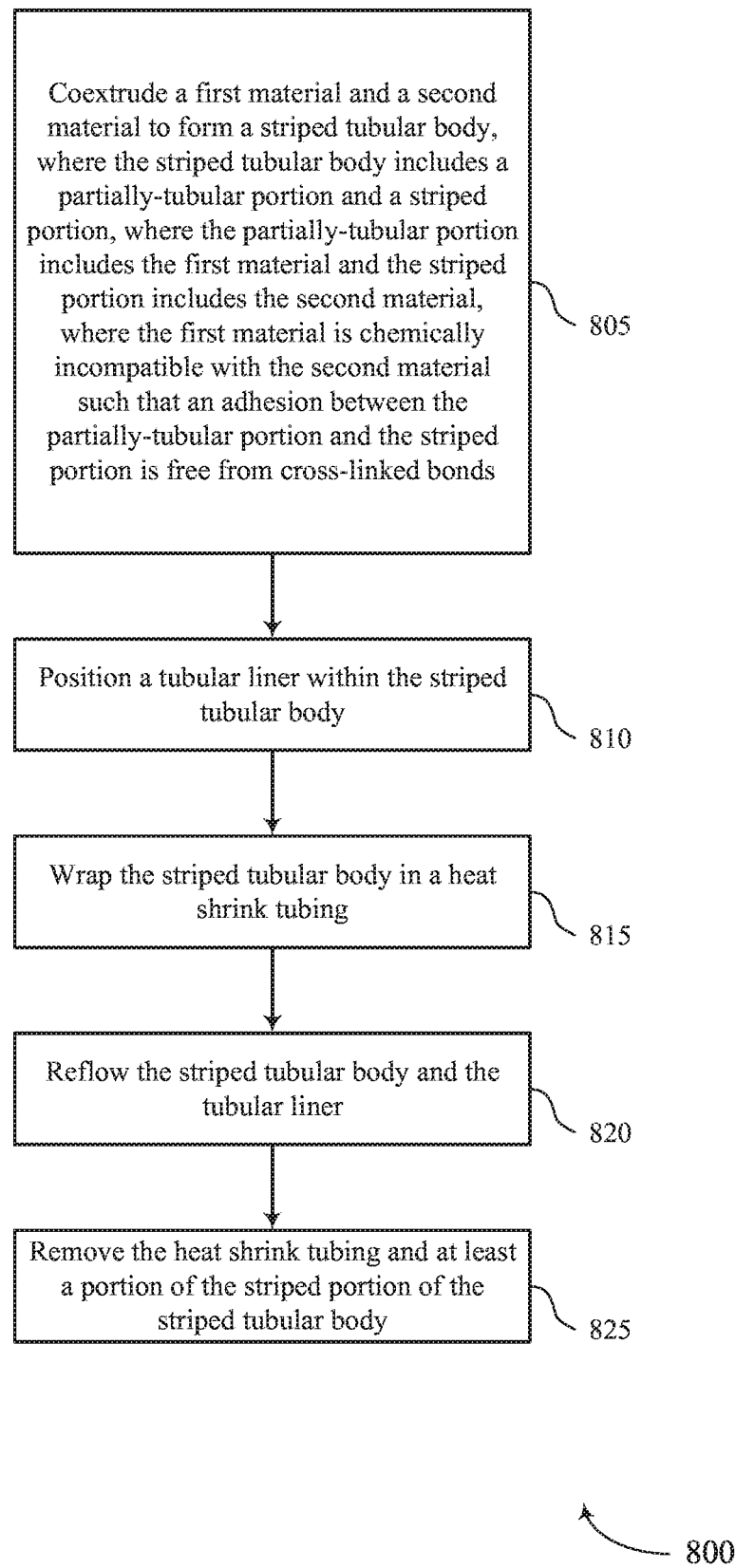
FIGS. 8-11 illustrate flow diagrams of methods of forming a sheath in accordance with aspects of the present disclosure.

FIG. 8 illustrates a flowchart of a method 800 for forming a sheath in accordance with aspects of the present disclosure. At block 805, the method may include coextruding a first material and a second material to form a striped tubular body, where the striped tubular body includes a partially-tubular portion and a striped portion, where the partially-tubular portion includes the first material and the striped portion includes the second material, where the first material is chemically incompatible with the second material such that an adhesion between the partially-tubular portion and the striped portion is free from cross-linked bonds. The striped tubular body may be an example of the striped tubular body of the sheaths described with reference to FIGS. 2-7. For example, as described above, the first material may be PEBA and the second material may be HDPE.

At block 810, the method may include positioning a tubular liner within the striped tubular body. The tubular liner may be an example of any of the tubular liners described with reference to FIGS. 2-7. For example, as described above, the tubular liner may be made from PTFE. In some examples, positioning a tubular liner within the striped tubular body may include loading the liner onto a mandrel and then loading the striped tubular body over the liner.

At block 815, the method may include wrapping the striped tubular body in a heat shrink tubing. At block 820, the method may include reflowing the striped tubular body and the tubular liner. In some examples, the process of reflowing may include using hot air or a glow ring. It may be appreciated that the temperatures and durations associated with the reflow process may depend on the material compositions and sizes of the striped tubular body and the tubular liner.

At block 825, the method may include removing the heat shrink tubing and at least a portion of the striped portion of the striped tubular body. As discussed above, in some examples, all of the striped portion may be removed, leaving a channel along the longitudinal direction of the tubular body. In other examples, only a portion of the striped portion is removed. In yet other examples, the striped portion may be kept on the tubular body.

Figure 9:
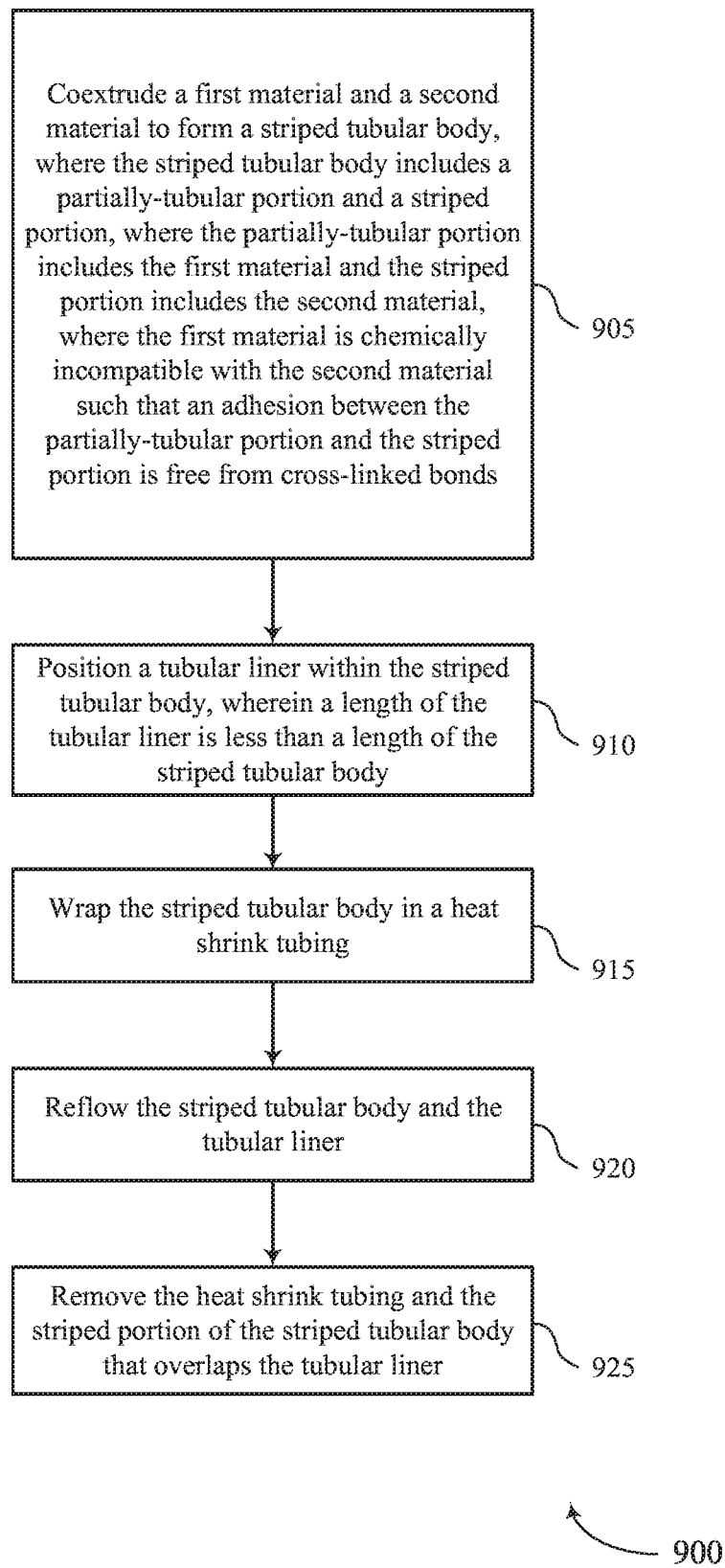

FIG. 9 illustrates a flowchart of a method 900 for forming a sheath in accordance with aspects of the present disclosure.

At block 905, the method may include coextruding a first material and a second material to form a striped tubular body, where the striped tubular body includes a partially-tubular portion and a striped portion, where the partially-tubular portion includes the first material and the striped portion includes the second material, where the first material is chemically incompatible with the second material such that an adhesion between the partially-tubular portion and the striped portion is free from cross-linked bonds. The striped tubular body may be an example of the striped tubular body of the sheaths described with reference to FIGS. 2-7. For example, as described above, the first material may be PEBA and the second material may be HDPE.

At block 910, the method may include positioning a tubular liner within the striped tubular body. In some examples, the length of the tubular liner may be less than a length of the striped tubular body. For example, the tubular liner may be an example of the tubular liner described with reference to FIG. 5. As described above, the tubular liner may be made from PTFE. In some examples, positioning a tubular liner within the striped tubular body may include loading the liner onto a mandrel and then loading the striped tubular body over the liner.

At block 915, the method may include wrapping the striped tubular body in a heat shrink tubing. At block 920, the method may include reflowing the striped tubular body and the tubular liner. In some examples, the process of reflowing may include using hot air or a glow ring. It may be appreciated that the temperatures and durations associated with the reflow process may depend on the material compositions and sizes of the striped tubular body and the tubular liner.

At block 925, the method may include removing the heat shrink tubing and at least a portion of the striped portion of the striped tubular body. For example, only the portion of the striped portion that overlaps the tubular liner may be removed, as described with reference to FIG. 5.

Figure 10:
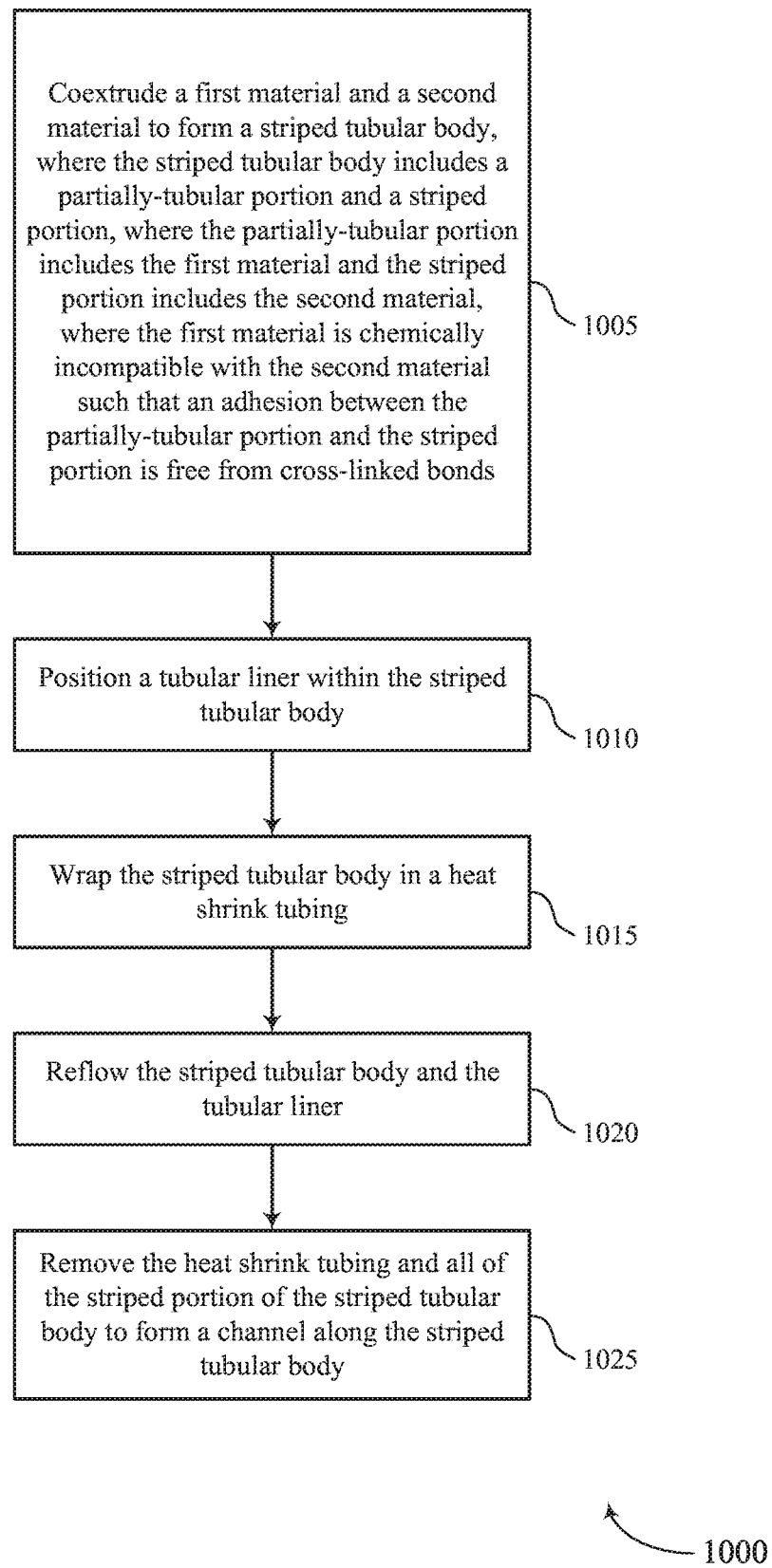

FIG. 10 illustrates a flowchart of a method 1000 for forming a sheath in accordance with aspects of the present disclosure. At block 1005, the method may include coextruding a first material and a second material to form a striped tubular body, where the striped tubular body includes a partially-tubular portion and a striped portion, where the partially-tubular portion includes the first material and the striped portion includes the second material, where the first material is chemically incompatible with the second material such that an adhesion between the partially-tubular portion and the striped portion is free from cross-linked bonds. The striped tubular body may be an example of the striped tubular body of the sheaths described with reference to FIGS. 2-7. For example, as described above, the first material may be PEBA and the second material may be HDPE.

At block 1010, the method may include positioning a tubular liner within the striped tubular body. The tubular liner may be an example of any of the tubular liners described with reference to FIGS. 2-7. For example, as described above, the tubular liner may be made from PTFE. In some examples, positioning a tubular liner within the striped tubular body may include loading the liner onto a mandrel and then loading the striped tubular body over the liner.

At block 1015, the method may include wrapping the striped tubular body in a heat shrink tubing. At block 1020, the method may include reflowing the striped tubular body and the tubular liner. In some examples, the process of reflowing may include using hot air or a glow ring. It may be appreciated that the temperatures and durations associated with the reflow process may depend on the material compositions and sizes of the striped tubular body and the tubular liner.

At block 1025, the method may include removing the heat shrink tubing and all of the striped portion of the striped tubular body to form a channel along the striped tubular body. The channel may expose the liner along the length of the striped tubular body.

Figure 11:
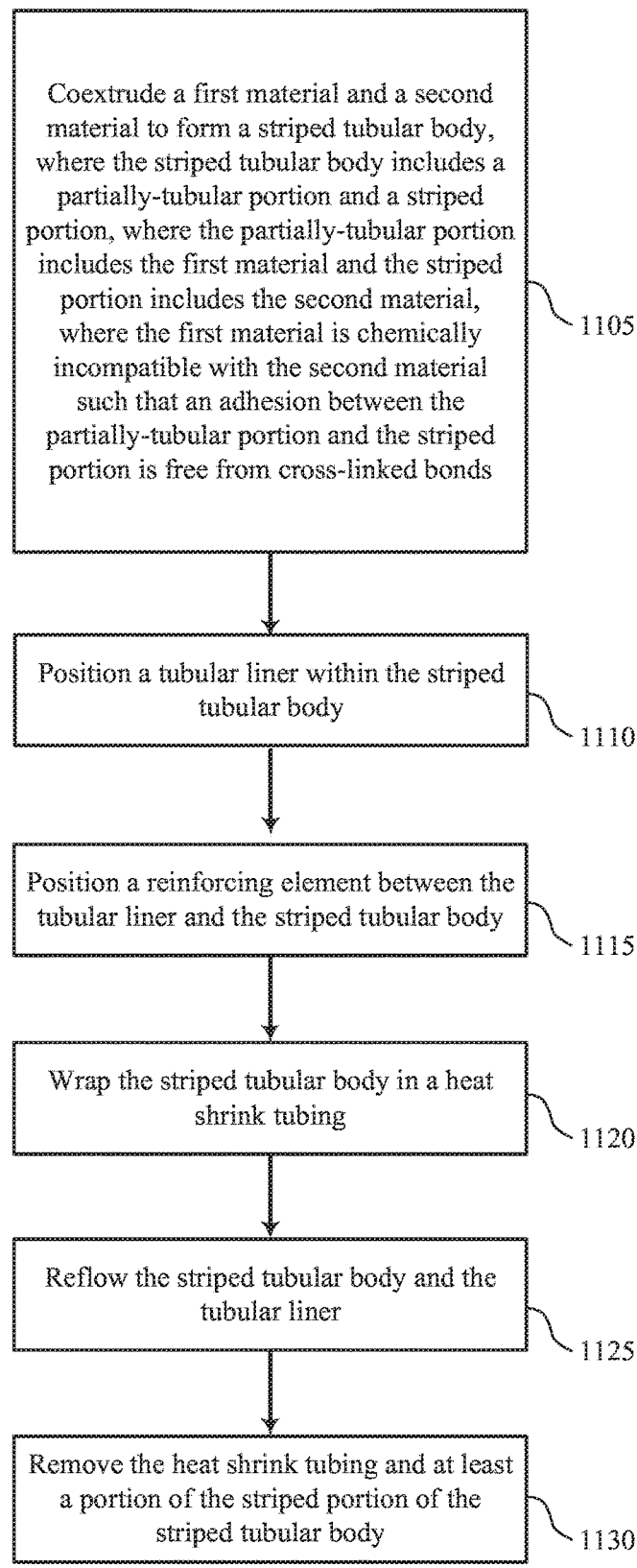

FIG. 11 illustrates a flowchart of a method 1100 for forming a sheath in accordance with aspects of the present disclosure. At block 1105, the method may include coextruding a first material and a second material to form a striped tubular body, where the striped tubular body includes a partially-tubular portion and a striped portion, where the partially-tubular portion includes the first material and the striped portion includes the second material, where the first material is chemically incompatible with the second material such that an adhesion between the partially-tubular portion and the striped portion is free from cross-linked bonds. The striped tubular body may be an example of the striped tubular body of the sheaths described with reference to FIGS. 2-7. For example, as described above, the first material may be PEBA and the second material may be HDPE.

At block 1110, the method may include positioning a tubular liner within the striped tubular body. The tubular liner may be an example of any of the tubular liners described with reference to FIGS. 2-7. For example, as described above, the tubular liner may be made from PTFE. In some examples, positioning a tubular liner within the striped tubular body may include loading the liner onto a mandrel and then loading the striped tubular body over the liner.

At block 1115, the method may include positioning a reinforcing element between the tubular liner and the striped tubular body. In some examples, the reinforcing element may be loaded onto the mandrel over the liner before the striped tubular body is loaded. In other examples, the reinforcing element may be loaded onto a mandrel before the liner and striped tubular body are loaded onto the mandrel. As described above, the reinforcing element may include a braided cage structure or a coiled wire structure.

At block 1120, the method may include wrapping the striped tubular body in a heat shrink tubing. At block 1125, the method may include reflowing the striped tubular body and the tubular liner. In some examples, the process of reflowing may include using hot air or a glow ring. Due to the reflow process, the material of the striped tubular body and liner may melt around and encapsulate the reinforcing element. It may be appreciated that the temperatures and durations associated with the reflow process may depend on the material compositions and sizes of the striped tubular body and the tubular liner.

At block 1130, the method may include removing the heat shrink tubing and at least a portion of the striped portion of the striped tubular body. As discussed above, in some examples, all of the striped portion may be removed, leaving a channel along the longitudinal direction of the tubular body. In other examples, only a portion of the striped portion is removed. In yet other examples, the striped portion may be kept on the tubular body.

It should be noted that these methods describe possible implementation, and that the operations and the steps may be rearranged or otherwise modified such that other implementations are possible. In some examples, aspects from two or more of the methods may be combined. For example, aspects of each of the methods may include steps or aspects of the other methods, or other steps or techniques described herein.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed herein.

While several embodiments of the present disclosure have been described and illustrated herein, those of ordinary skill in the art will readily envision a variety of other means or structures for performing the functions or obtaining the results or one or more of the advantages described herein, and each of such variations or modifications is deemed to be within the scope of the present disclosure. More generally, those skilled in the art will readily appreciate that all parameters, dimensions, materials, and configurations described herein are meant to be exemplary and that the actual parameters, dimensions, materials, or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, or method described herein. In addition, any combination of two or more such features, systems, articles, materials, kits, or methods, if such features, systems, articles, materials, kits, or methods are not mutually inconsistent, is included within the scope of the present disclosure.

All definitions, as defined and used herein, should be understood to control over dictionary definitions, definitions in documents incorporated by reference, or ordinary meanings of the defined terms.

The indefinite articles "a" and "an," as used herein in the specification and in the claims, unless clearly indicated to the contrary, should be understood to mean "at least one." Also, as used herein, including in the claims, "or" as used in a list of items (for example, a list of items prefaced by a phrase such as "at least one of" or "one or more") indicates an inclusive list such that, for example, a list of at least one of A, B, or C means A or B or C or AB or AC or BC or ABC (i.e., A and B and C).

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

What is claimed is:
1. A sheath, comprising:
a partially-tubular first portion comprising a first material;

a tubular liner that extends within the first portion from a first end of the first portion to a first length less than a length of the first portion; and a second portion comprising a second material that extends from a second end of the first portion to a second length less than the length of the first portion, wherein the second portion at least partially overlaps with the tubular liner, wherein the second portion is adhered to the first portion along the second length to form a tubular body and removed from the first length such that the tubular liner is exposed along the first length, wherein the first material is chemically incompatible with the second material such that the adhesion between the first portion and second portion is free from cross-linked bonds.

2. The sheath of claim 1, wherein the second portion is oriented as a stripe along a longitudinal axis of the tubular body.

3. The sheath of claim 1, wherein the first material comprises polyether block amide (PEBA) and the second material comprises high-density polyethylene (HDPE).

4. The sheath of claim 1, wherein the tubular liner comprises polytetrafluoroethylene (PTFE).

5. The sheath of claim 1, further comprising:
a reinforcing element comprising a frame embedded within the first portion.

6. The sheath of claim 5, wherein the reinforcing element comprises a partially-tubular body with a channel that aligns with the second portion.

7. The sheath of claim 5, wherein the reinforcing element comprises a coiled frame.

8. The sheath of claim 5, wherein the reinforcing element comprises a braided frame.

9. A stent deployment system, comprising:
a sheath comprising:
a partially-tubular first portion comprising a first material;
a tubular liner that extends within the first portion from a first end of the first portion to a first length less than a length of the first portion; and
a second portion comprising a second material that extends from a second end of the first portion to a second length less than the length of the first portion, wherein the second portion at least partially overlaps with the tubular liner, wherein the second portion is adhered to the first portion along the second length to form a tubular body and removed from the first length such that the tubular liner is exposed along the first length, wherein the first material is chemically incompatible with the second material such that the adhesion between the first portion and second portion is free from cross-linked bonds;
a guidewire lumen slidably disposed within the sheath, wherein the guidewire lumen comprises a distal tip with an outer diameter that is greater than an inner diameter of the tubular body; and
a tubular stent disposed between the guidewire lumen and an inside surface of the sheath.

10. The stent deployment system of claim 9, further comprising:
a guidewire slidably disposed within the guidewire lumen.

* * * * *